United States Patent [19]

Rose

[11] Patent Number: 5,279,833

[45] Date of Patent: Jan. 18, 1994

[54] LIPOSOMAL TRANSFECTION OF NUCLEIC ACIDS INTO ANIMAL CELLS

[75] Inventor: John K. Rose, Guilford, Conn.

[73] Assignee: Yale University, New Haven, Conn.

[21] Appl. No.: 504,498

[22] Filed: Apr. 4, 1990

[51] Int. Cl.$^5$ .................. A61K 37/22; C07H 21/02; C07H 21/04

[52] U.S. Cl. .................. 424/450; 435/6; 435/7.21; 435/7.25; 435/7.23; 436/71; 558/169; 558/172; 564/282; 564/291; 564/463

[58] Field of Search .............. 424/450; 536/27; 435/6, 435/240.2; 436/71; 558/169, 172; 564/282, 291, 463

[56] References Cited

U.S. PATENT DOCUMENTS 4,897,355  1/1990  Eppstein et al. .................. 435/240.2
4,946,787  8/1990  Eppstein et al. .................. 435/240.2

OTHER PUBLICATIONS

Whitt et al. "Transfect Ace TM Reagent; Transient Transfection Frequencies >9090," *Focus* 13(1): 8–12, 1991. (Publication of Life Technologies, Inc.).

Felgner et al. Proc. West. Pharmacol. Soc. 32: 115–121, 1989.

Sigma Chemical Catalog 1990, St. Louis, Mo.; pp. 100, 272, 672, 826–827, 829–833, 945, and 960.

Pinnadwage et al. Biochim. Biophys. Acta 985: 33–37, 1989.

Philip L. Felgner et al, Lipofection: A Highly Efficient, Lipid-Mediated DNA-Transfection Procedure, Proc. Natl. Acad. Sci. USA, 84, 7413–7417 (1987).

T. R. Fuerst et al, Proc. Nat. Acad. Sci. USA, 83, 8122–8126 (1986).

A. S. Shaw et al, Proc. Natl. Acad. Sci. USA, 85, 7592–7596 (1988).

M. Whitt et al, J. Virol., 63, 3569–3578 (1989).

A. Shaw et al, Cell, 59, 627–636 (1989).

F. L. Graham et al, Virology, 52, 456–467, (1973).

P. L. Felgner et al, Cationic Liposome-Medicated Transfection, Nature, 337, 387–388, (1989).

J-P. Behr et al, Proc. Natl. Acad. Sci., USA, 86, 6982–6986, (1989).

L. Lefrancois et al, Virology, 121, 157–167, (1982).

J. K. Rose et al, Cell, 34, 513–524 (1983).

Y. Quzman, Cell, 23, 175–182, (1981).

O. Elroy-Stein et al, Proc. Natl. Acad. Sci. USA, 86, 6126–6130 (1989).

*Primary Examiner*—Ronald W. Griffin
*Assistant Examiner*—Gary L. Kunz
*Attorney, Agent, or Firm*—Frishauf, Holtz, Goodman & Woodward

[57] ABSTRACT

A reagent for introducing a nucleic acid into an animal cell. The reagent comprises (a) a neutral lipid such as dioleoylphosphatidylethanolamine and (b) a cationic lipid selected from the group consisting of an ammonium salt such as dimethyldioctadecylammonium bromide or cetyldimethylethylammonium bromide, an amine such as stearylamine, and a benzethonium salt such as methylbenzethonium chloride

11 Claims, 5 Drawing Sheets

LIPOSOMAL TRANSFECTION OF NUCLEIC ACIDS INTO ANIMAL CELLS

GOVERNMENT RIGHTS

This invention was made with United States Government support under Grant AI 24345-03 from the NIH. The United States Government has certain rights in this invention.

BACKGROUND OF THE INVENTION

1. Field of the Invention

The present invention concerns a reagent and a method for introducing nucleic acid into animal cells.

2. Background Information

There are currently four major reagents or methods used to introduce DNA into animal cells. These are (1) CaPO$_4$-DNA precipitates, (2) DEAE dextran-DNA complexes, (3) electroporation and (4) "LIPOFECTIN" TM reagent, a transfection reagent marketed by BRL (Life Technologies, Inc., Gaithersburg, Md).

Recently, a liposome-mediated transfection protocol ("LIPOFECTION" TM) has been reported for the introduction of DNA into animal cells (Philip L. Felgner, Thomas R. Gadek, Marilyn Holm, Richard Roman, Hardy W. Chan, Michael Wenz, Jeffrey P. Northrop, Gordon M. Ringold and Mark Danielsen, "Lipofection: A Highly Efficient, Lipid-Mediated DNA-Transfection Procedure," Proc. Natl. Acad. Sci. USA, 84, 7413-7417 (1987)). This protocol uses the synthetic cationic lipid DOTMA (N-[1-(2,3-dioleyloxy)propyl] -N,N,N-trimethylammonium chloride). Liposomes composed of DOTMA and a neutral lipid PtdEtn (dioleoylphosphatidylethanolamine) form stable complexes with DNA, and deliver DNA into several eukaryotic cells with higher efficiency and reproducibility than other methods.

A transient expression system that requires transfected DNA to be present in the cytoplasm has recently been described by T.R. Fuerst, E.G. Niles, W. Studier and B. Moss, Proc. Natl. Acad. Sci. USA, 83, 8122-8126 (1986). This system is based on use of a recombinant vaccinia virus that synthesizes bacteriophage T7 RNA polymerase. The plasmid DNA containing the gene of interest under control of the T7 promoter is transfected as a CaPO$_4$ precipitate into the cytoplasm of the vaccinia infected cells where it is transcribed efficiently by the T7 RNA polymerase. The mRNA derived from the transfected gene can be as much as 10% of the total cytoplasmic RNA. This system has facilitated studies of viral glycoprotein translocation (A.S. Shaw, P.J.M. Rottier and J.K. Rose, Proc. Natl. Acad. Sci. USA, 85, 7592-7596, (1988)) and virus assembly (M. Whitt, L. Chong and J.K. Rose, J. Virol., 63, 3569-3578 (1989)), and has allowed for the definition of interacting domains of the lymphocyte glycoprotein CD4 and an intracellular tyrosine protein kinase (A. Shaw, K. Amrein, C. Hammond, D.F. Stern, B.M. Sefton and J.K. Rose, Cell, 59, 627-636 (1989)). A major difficulty with this system was the lack of reproducibility of the transfection step using CaPO$_4$ precipitates of DNA (Fuerst et al, Proc. Natl. Acad. Sci. USA, 83, 8122-8126, (1986) and F.L. Graham and A.J. Van Der Eb, Virology, 52, 456-467, (1973)). The percentage of cells expressing protein showed a high degree of day-to-day variability, some plasmid DNA preparations were inactive for unknown reasons, and it was not possible to use impure plasmid DNA preparations containing large amounts of RNA (DNA from minipreps).

The variability in the transfection was overcome by using lipofection instead of the CaPO$_4$ procedure (M. Whitt et al, J. Virol., 63, 3569-3578, (1989)) and a threefold increase over the best expression levels obtained with CaPO$_4$ was found.

A major drawback to the DOTMA transfection procedure is that the compound itself is not commercially available, and the preformed liposomes containing DOTMA ("LIPOFECTIN" TM reagent, Life Technologies, Inc., Gaithersburg, Md.) are too expensive for large scale use in transient assays. The cost of lipofection is prohibitive ($145/ml or about $10 per transfection) to laboratories, especially to laboratories which perform thousands of transfections per year.

P.L. Felgner and G.M. Ringold, "Cationic Liposome-Medicated Transfection," Nature, 337, 387-388, (1989) at page 387 report that liposomes comprised of stearylamine or dioctaldecyl-dimethylammonium bromide were inactive in transfection assays.

J.-P. Behr, B. Demeneix, J-P. Loeffler and J.P. Mutul, Proc. Natl. Acad. Sci., USA, 86, 6982-6986, (1989) described a transfection procedure using compacted lipopolyamine-coated plasmids.

It would be advantageous to have a reagent and method for introducing nucleic acids into animal cells using readily available and relatively inexpensive compounds.

SUMMARY OF THE INVENTION

It is an object of the present invention to introduce nucleic acids into animal cells using relatively available and relatively inexpensive reagents. This object, as well as other objects, aims and advantages are achieved by the present invention.

The present invention concerns a reagent for introducing nucleic acids into an animal cell comprising
a. a neutral lipid, for example, dioleyl phosphatidylethanolamine, and
b. a cationic lipid selected from the group consisting of
(1) an ammonium salt of the formula

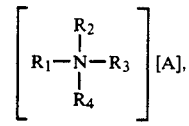

wherein R$_1$ is a straight hydrocarbon chain of C$_{14}$ to C$_{18}$ that is saturated or unsaturated,
R$_2$, R$_3$ and R$_4$ are, independently of each other, hydrogen, a straight hydrocarbon chain of C$_1$ to C$_{18}$ that is saturated or unsaturated or an aryl, e.g., benzyl or phenyl, and A is an anion,
(2) an amine of the formula

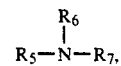

wherein R$_5$ is a straight chain of C$_{14}$ to C$_{18}$ that is saturated or unsaturated and wherein R$_6$ and R$_7$, independently of each other, are hydrogen or C$_1$ to C$_5$ alkyl and
(3) a benzethonium salt of the formula

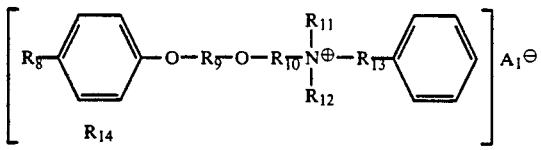

wherein $R_8$ is a straight chain or branched $C_1$-$C_{10}$-alkyl,
$R_9$ is a chain $C_1$-$C_{10}$-alkyl,
$R_{10}$ is a chain $C_1$-$C_{10}$-alkyl,
$R_{11}$ is a chain $C_1$-$C_{10}$-alkyl,
$R_{12}$ is a chain $C_1$-$C_{10}$-alkyl,
$R_{13}$ is a chain $C_1$-$C_{10}$-alkyl,
$R_{14}$ is a chain $C_1$-$C_{10}$-alkyl and
$A_1^\ominus$ is an anion.

The present invention also concerns a method for introducing a nucleic acid into an animal cell comprising a. mixing nucleic acid with a reagent as described above to form a liposome or lipid micelles and b. contacting the resultant liposome or lipid micelles with an animal cell.

The present invention further relates to a complex between a nucleic acid and the reagent as defined above. Still further, the present invention is directed to such complex further comprising a liposome or lipid micelles.

BRIEF DESCRIPTION OF THE DRAWINGS

For the purpose of illustrating the invention there is shown in the drawings forms which are presently preferred. It is to be understood, however, that the present invention is not limited to the precise arrangements and instrumentalities depicted in the drawings.

FIG. 1A is a profile for a control (mock transfection). FIG. 1B is a profile for pARG transfected (pARG is a plasmid that encodes a viral glycoprotein).

DETAILED DESCRIPTION OF THE INVENTION

Figure 1A:
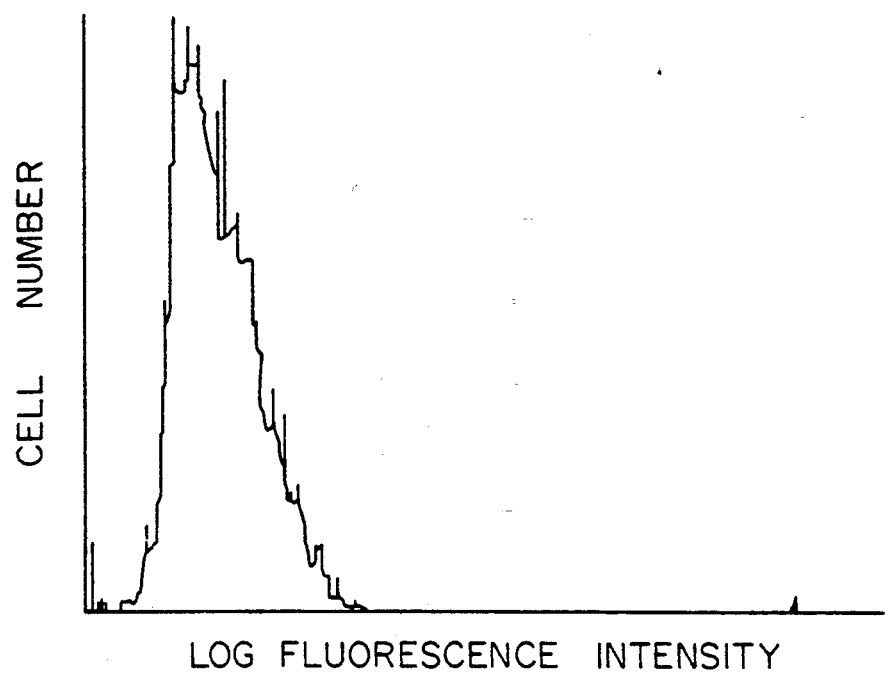
FIG. 1A and 1B depict flow cytometry profiles showing a high frequency of VSV glycoprotein expression on the surface of HeLa cells.

The invention concerns a reagent and a method for introducing nucleic acid into animal cells with very high efficiency. The reagent is composed of a cationic lipid (detergent), for example, dimethyldioctadecylammonium bromide, and a neutral lipid, for example, dioleoyl phosphatidylethanolamine. Liposomes are formed from these two compounds. Nucleic acid, e.g., DNA or RNA, is mixed with the preformed liposomes in medium and added to cells, e.g., on a tissue culture dish. This results in nucleic acid, e.g., DNA, delivery into the cells with high efficiency.

Non-limiting examples of other neutral lipids for use in the present invention include the following: phospholipid-related materials such as lecithin, lysolecithin, lysophosphatidylethanolamine, phosphatidylserine, phosphatidylinositol, sphinogomyelin, cephalin, cardiolipin, phosphatidic acid, cerebrosides, acetylphosphate, dioleoylphosphatidylcholine (DOPE), dipalmitoylphosphatidylcholine, dioleoylphosphatidylglycerol (DOPC), dipalmitoylphosphatidylglycerol, dioleoylphosphatidylethanolamine (DOPE), palmitoyloleoylphosphatidylcholine (POPC), palmitoyloleoylphosphatidylethanolamine (POPE), dioleoylphosphatidylethanolamine 4-(N-maleimidomethyl) cyclohexane-1-carboxylate (DOPE-MAL), diheptadecanoyl phosphatidylethanolamine, dilauroylphosphatilylethanolamine, dimyristoylphosphatidylethanolamine, distearoyl phosphatidylethanolamine, beta-linoleoyl-gammapalmitoyl phosphatidylethanolamine and beta-oleoyl-gammapalmitoyl phosphatidylethanolamine.

The cationic lipid for use in the present invention is (1) an ammonium salt of the formula

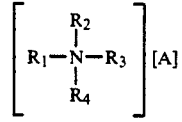

wherein $R_1$ is a straight hydrocarbon chain of $C_{14}$ to $C_{18}$ that is saturated or unsaturated, $R_2$, $R_3$ and $R_4$ are, independently of each other, hydrogen, a straight hydrocarbon chain of $C_1$-$C_{18}$ that is saturated or unsaturated, preferably $C_1$-$C_5$-alkyl or $C_{18}$a-alkyl or an aryl, e.g., a benzyl or phenyl and A is an anion, for example, a halogen, for example, Br, Cl, I or F, preferably Br, or a sulfate, nitrite or nitrate, wherein preferred embodiments of such salt are cetyldimethyethylammonium bromide of the formula $CH_3(CH_2)_{15}N(CH_3)_2(C_2H_5)Br$ and dimethyldioctadecylammonium bromide (DDAB) of the formula $((CH_3)(CH_2)_{17})_2N(CH_3)_2Br$, (2) an amine of the formula

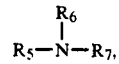

wherein $R_5$ is a straight chain of $C_{14}$ to $C_{18}$ that is saturated or unsaturated and wherein $R_6$ and $R_7$, independently of each other, are hydrogen or $C_1$ to $C_5$ alkyl, preferably the amine is stearylamine of the formula $CH_3(CH_2)_{17}NH_2$, or (3) a benzethonium salt of the formula

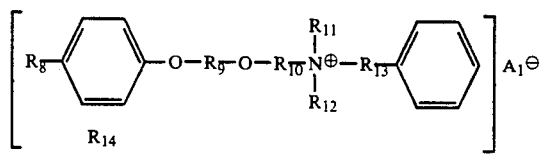

wherein $R_8$ is a straight chain or branched $C_1$-$C_{10}$-alkyl,
$R_9$ is a $C_1$-$C_{10}$-alkyl,
$R_{10}$ is a $C_1$-$C_{10}$-alkyl,
$R_{11}$ is a $C_1$-$C_{10}$-alkyl,
$R_{12}$ is a $C_1$-$C_{10}$-alkyl,
$R_{13}$ is a $C_1$-$C_{10}$-alkyl, $R_{14}$ is a $C_1$-$C_{10}$-alkyl and $A_1^\ominus$ is an anion, for example a halogen, for example, Br, Cl, I or F, preferably Cl, or a sulfate, nitrate or nitrate, preferably the benzethonium salt is methylbenzethonium chloride of the formula

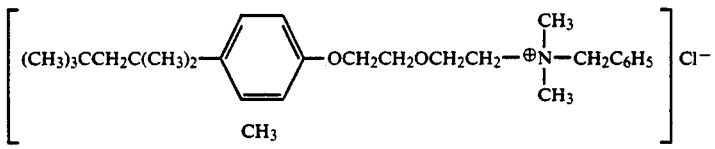

(N,N-dimethyl-N-[2-[2-methyl-4-(1,1,3,3-tetramethylbutyl)-phenoxy]ethoxy]ethyl]benzenemethanaminium chloride).

The present invention also encompasses substituted forms of the ammonium salts, amines and benzethonium salts as described above, wherein the use of such substituted forms in the reagent functions to allow the introduction of nucleic acid into an animal cell.

The ratio of cationic lipid to neutral lipid can be widely varied, depending on the particular cationic lipid employed. Thus for cetyldimethylethylammonium bromide and methylbenzethonium chloride the ratio can be 3/30 to 12/30; for dimethyldioctadecylammonium bromide the ratio can be 6/30 to 12/30; and for stearylamine, the ratio can be 0.3/30 to 30/30.

The ratio of nucleic acid, e.g., DNA, to cationic lipid should not be so high as to saturate the positive charges on the liposomes, which could result in that the liposomes would not bind the cell surface.

Animal cells for use in the present invention include cells from humans and non-human warm blooded animals. Erythrocytes, for example, can be employed. Also baby hamster kidney (BHK) cells, AtI 20 cells, RK-13 cells and Madin-Darby canine kidney (MDCK) cells can be used in the present invention.

Although cytoplasmic gene expression is preferred, gene expression in the cell nucleus can be conducted according to the invention.

Nucleic acid as used in this application includes DNA, RNA and oligonucleotides of DNA and RNA.

The nucleic acid, e.g., DNA or RNA, coding for specific genes of interest may be retrieved, without undue experimentation, from the GenBank of EMBL DNA libraries. Such sequences may include coding sequences, for example, the coding sequences for structural proteins, hormones, receptors and the like, and the DNA sequences for other DNAs of interest, for example, transcriptional and translational regulatory elements (promoters, enhancers, terminators, signal sequences and the like), vectors (integrating or autonomous) and the like. Non-limiting examples of DNA sequences which may be introduced into cells with the reagent of the invention include those sequences coding for fibroblast growth factor (WO 87/01728); ciliary neurotrophic factor (Lin et al, *Science*, 246:1023–1025 (1989); human interferon-α receptor (Uze, G. et al, *Cell*, 60:225–235 (1990); the interleukins and their receptors (reviewed in Mizal, S.B., FASEB J., 3:2379–2388 (1989); hybrid interferons (see European Patent Application No. 051,873); the RNA genome of human rhinovirus (see Callahan, P.L., *Proc. Natl. Acad. Sci. (USA)*, 82:732–736 (1985)); antibodies including chimeric antibodies (see Cabilly et al, U.S. Pat. No. 4,816,567); reverse transcriptase (see Moelling, K., et al. *J. Virol.*, 32:370–378 (1979)); human CD4 and soluble forms thereof (Maddon et al, *Cell*, 47:333–348 (1986); PCT Application Publication Nos. WO 88/01304 (1988) and WO 89/01940 (1989)). See also Seed, B. et al. European Patent Application Publication No. 330,191, who disclose a rapid immunoselection cloning method which is useful for the cloning of a large number of important proteins. The disclosures of the references cited above are fully incorporated by reference herein.

The present invention can be employed for the introduction of DNA, for example, into animal cells for research purposes. The most common reason for doing this is to obtain transient or permanent expression of DNA in established animal cell lines. This is done on a daily basis in thousands of laboratories worldwide.

The present invention can also be employed in gene therapy, e.g., to treat genetic diseases in humans and nonhuman warm blooded animals. For example, a "missing gene" can be introduced in the bone marrow of a patient by the present invention.

The invention can further be used to treat infectious diseases, e.g., AIDS, by blocking infection.

Transformation/Transfection is defined as follows: the introduction of DNA or RNA into cells in such a way as to allow gene expression.

Liposomes consist of spheres of lipid bilayers (two-molecules thick) that enclose an aqueous medium.

Liposomes can generally be formed by sonicating a lipid in a aqueous medium, by resuspension of dried lipid layers in a buffer or by dialysis of lipids dissolved in an organic solvent against a buffer of choice.

Phospholipids form closed, fluid-filled spheres when they are mixed with water, in part because the molecules are amphipathic: they have a hydrophobic (water-insoluble) tail and a hydrophilic (water-soluble), or "polar," head. Two fatty acid chains containing up to about 24 carbon atoms generally make up the hydrophobic tail of most naturally occurring phospholipid molecules. Phosphoric acid bound to any of several water-soluble molecules composes the hydrophilic head. When a high enough concentration of phospholipids is mixed with water, the hydrophobic tails spontaneously herd together to exclude water, whereas the hydrophilic heads bind to water.

The result is a bilayer in which the fatty acid tails point into the membrane's interior and the polar head groups point outward. The polar groups at one surface of the membrane point toward the liposome's interior and those at the other surface point toward the external environment. As a liposome forms, any water-soluble molecules that have been added to the water are incorporated into the aqueous spaces in the interior of the spheres, whereas any lipid-soluble molecules added to the solvent during vesicle formation are incorporated into the lipid bilayer.

Liposomes typically range in diameter from 250 angstrom units to several micrometers (the diameter of a red blood cell is roughly 10 micrometers) and are usually suspended in a solution. They have two standard forms: "onion-skinned" multilamellar vesicles (MLV's), made up of several lipid bilayers separated by fluid, and unilamellar vesicles, consisting of a single bilayer surrounding an entirely fluid core. The unilamellar vesicles are typically characterized as being small (SUV's) or large (LUV's). The unilamellar vesicles are preferred in the present invention.

Under appropriate circumstances liposomes can adsorb to almost any cell type. Once they have adsorbed the spheres, liposomes may be endocytosed, or swallowed up, by some cells. Adsorbed liposomes can also exchange lipids with cell membranes and may at times be able to fuse with cells. When fusion takes place, the liposomal membrane is integrated into the cell membrane and the aqueous contents of the liposome merge with the fluid in the cell.

Endocytosis of liposomes occurs in a limited class of cells; those that are phagocytic, or able to ingest foreign particles. When phagocytic cells take up liposomes, the cells move the spheres into subcellular organelles known as lysosomes, where the liposomal membranes are thought to be degraded. From the lysosome, the liposomal lipid components probably migrate outward to become part of the cell's membranes and other liposomal components that resist lysosomal degradation (such as certain medications) may enter the cytoplasm.

Lipid exchange involves the transfer of individual lipid molecules from the liposome into the plasma membrane (and vice versa); the aqueous contents of the liposome do not enter the cell. For lipid exchange to take place, the liposomal lipid must have a particular chemistry in relation to the target cell. Once a liposomal lipid joins the cell membrane it can either remain in the membrane for a long time or be redistributed to a variety of intracellular membranes.

In very dilute solutions, lipid micelles may form instead of liposomes.

With respect to screening procedures described herein, alternative components active in transfection could be screened by substituting them for PtdEtn in the preparation of liposomes containing cationic lipids. These liposomes would then be used to transfect cells with plasmid DNA encoding a protein that is easily assayed (for example the VSV glycoprotein). The frequency of gene expression in cells would be determined by flow cytometry as depicted in FIG. 1 and FIG. 5.

The invention will now be described with reference to the following non-limiting examples.

EXAMPLES

MATERIALS

LIPIDS

L-α-dioleoylphosphatidylethanolamine (PtdEtn), stearylamine, cetyldimethlyethyl-ammonium bromide, dimethyldioctadecylammonium bromide (DDAB), and methylbenzethonium chloride (N,N-dimethyl-N-[2-(2-[methyl-4-(1,1,3,3-tetramethylbutyl)-phenoxy]ethoxy)ethyl]benzenem chloride), were purchased from Sigma Chemical Co., St. Louis, Mo. "LIPOFECTIN"™ reagent was purchased from Life Technologies, Inc., Gaithersberg, Md.

CELLS AND MEDIA

HeLa cells were grown in Dubecco-Vogt's modified minimal essential medium (DMEM) containing 10% horse serum or 5% fetal calf serum. Baby Hamster Kidney (BHK) cells, AtT-20 cells, RK-13 cells, and Madin-Darby canine kidney cells (MDCK) cells were grown in DME containing 5% fetal calf serum.

EXAMPLE 1: LIPOSOME PREPARATION

Dioleoylphosphatidylethanolamine (PtdEtn) was supplied as a 10 mg/ml solution in $CHCl_3$. The other lipids were dissolved in $CHCl_3$ at 100 mg/ml. Liposomes were typically prepared as follows. One mg of PtdEtn (0.1 ml of a 10 mg/ml solution) was combined with varying amounts of each cationic lipid (e.g., 0.4 mg DDAB) and the solution was evaporated to dryness overnight in a Speed Vac Concentrator (Savant). Liposomes were prepared by resuspending the lipids in 1 ml sterile deionized water and sonicating on ice using an Ultrasonics Sonicator (microprobe, 50V setting) until the solution was almost clear This typically required 5–10 minutes, with pausing every 10–15 seconds to prevent overheating. Because applicants observed variability in the transfection frequencies obtained with different batches of liposomes sonicated to different extents, a procedure was adopted of sonicating DDAB/PtdEtn (0.4 mg/ml and 1 mg/ml, respectively) until a 1:10 dilution in distilled water gave an O.D. of 0.1 at 540 nm. Liposomes were stored at 4° C. and were stable for at least four months. were stable for at least four months.

EXAMPLE 2: TRANSFECTIONS

Plasmid DNA was normally purified by isopycnic banding in CsCl gradients. However, it was found that crude DNA preparations which had not been separated from RNA (minipreps) were also very effective. Cells to be transfected (typically $5 \times 10^5$ HeLa or BHK cells) were plated on 3 cm dishes. On the following day they were infected with vaccinia virus encoding the T7 RNA polymerase (Fuerst et al, *Proc. Natl. Acad. Sci. USA*, 83, 8122–8126 (1986)) at a multiplicity of 10 and incubated for 30 minutes at 37° C. in 0.5 ml DME. Details of individual transfections are given in the FIGURES. A typical transfection giving optimal expression in BHK or HeLa cells was performed as follows. Five μg of plasmid DNA were added to 1 ml of DMEM in a polystyrene tube followed by addition 30 μl of liposomes. This solution was mixed gently and then incubated at room temperature for 10 minutes to allow binding of DNA to liposomes. The vTF-7 inoculum was replaced with the liposome-DNA solution and incubated with the cells for 3 hours at 37° C. in a 5% $CO_2$ incubator. An additional 1 ml of DME with 10% fetal calf serum was then added without removing the transfection mixture. It was found that the DNA and liposome amount can be reduced at least two fold (2.5 μg DNA and 15 μl liposomes) without reducing the protein expression level significantly.

For transfection using $CaPO_4$-DNA precipitates, cells in 6 cm dishes were infected with VTF-7 as described above. After removing the inoculum, 4 ml of DME with 5% fetal bovine serum were added followed by 0.75 ml of $CaPO_4$-precipitated DNA containing 15 μg pARG DNA and 15 μg sonicated calf thymus DNA carrier (added dropwise). The $CaPO_4$-DNA suspension was prepared essentially as described in F.L. Graham and A.J. Van der Eb, *Virology*, 52, 456–467 (1973).

EXAMPLE 3: FLUORESCENCE MICROSCOPY

Indirect immunofluorescence was carried out on Hela and BHK cells six hours after transfection as described in J.K. Rose and J.E. Bergmann, *Cell*, 34, 513–524 (1983) with the following modifications. Fixed HeLa cells were incubated with rabbit anti-VSV serum (1:200), followed by FITC conjugated goat anti-rabbit immunoglobulin G (IgG) (1:50 dilution; Zymed Laboratories, San Francisco, Calif.) for detection of cell-surface G protein. For detection of G protein on the surface of BHK cells, a mouse monoclonal antibody (II, L. Lefrancois and D.S. Lyles, *Virology*, 121, 157-167 (1982)) was used with an FITC-conjugated goat anti-mouse second antibody. For determination of the percent of cells expressing, at least five random fields of cells were counted (250-500 cells) using a Nikon Microphot-FX fluorescence microscope equipped with a planapochromat 40x objective.

EXAMPLE 4: FLOW CYTOMETRY

BHK or HeLa cells were infected with vTF7-3 and transfected as described above with various ratios of DNA and cationic liposome suspensions. The cells were removed from the dish and fixed in suspension at 6 hours post-transfection. The cells were processed for flow cytometric analysis as described in M. Whitt, L. Chong and J.K. Rose, *J. Virol.*, 63, 3569-3578 (1989), except that in some experiments 0.5% bovine serum albumin was included during the antibody incubations.

EXAMPLE 5: RADIOLABELING AND IMMUNOPRECIPITATION

Four hours post-transfection, cells were metabolically labeled by incubation in methionine free DMEM containing [$^{35}$S]-methionine (25µCi/0.5 ml) for 30 minutes. Cells were lysed, and the VSV G protein was immunoprecipitated with a rabbit anti-VSV antibody as described in J. K. Rose and J.E. Bergmann, *Cell*, 34, 513-524 (1983). Immunoprecipitated proteins were analyzed by electrophoresis in 10% polyacrylamide gels in the presence of sodium dodecyl sulfate. Dried gels were subjected to autoradiography. For quantitation of radioactivity in the bands, films were scanned with a Hoeffer model GS300 densitometer and the peaks were integrated.

EXAMPLE 6: USE OF VARIOUS CATIONIC LIPIDS TO FORM LIPOSOMES To Mediate DNA Transfection To determine if cationic lipids other than DOTMA could form liposomes that would mediate DNA transfection into the cytoplasm of animal cells, an experiment was performed using four commercially available cationic lipids (see Table 1). These lipids were chosen because they had long alkyl chains, were relatively insoluble in water, and thus were not expected to act as strong detergents. Liposomes were formed by sonication with a constant amount of the neutral lipid, dioleyl-phosphatidylethanolamine (PtdEtn), and the amount of each cationic lipid was varied as indicated. The neutral lipid was added because of the previous report that it enhanced transfection of liposomes containing DOTMA (Felgner et al, *Proc. Natl. Acad. Sci USA*, 84, 7413-7417 (1987)). The vesicular stomatitis virus (VSV) glycoprotein (G) has been expressed from cloned DNA previously and is transported to the cell surface (Rose et al, *Cell*, 34, 513-524 (1983)). Plasmid DNA designated pARG (M. Whitt, L. Chong and J.K. Rose, *J. Virol.*, 63, 3569-3578 (1989)) containing a cDNA clone encoding the VSV G protein under control of the bacteriophage T7 promoter was mixed with the preformed liposomes and then added to cells. These cells had been infected with vTF-7 for 30 minutes prior to transfection. vTF-7 is a vaccinia virus recombinant which expresses the bacteriophage T7 RNA polymerase in the cytoplasm of infected cells (Fuerst et al, *Proc. Natl. Acad. Sci. USA*, 83, 8122-8126 (1986)). Six hours after transfection, cells were fixed with paraformaldehyde, labeled with fluorescent antibodies recognizing the VSV G protein, and counted using a fluorescence microscope to determine the percent of cells expressing the protein. Results of these initial experiments (Table 1) showed that all four of the compounds tested were effective in HeLa cells when used at an appropriate concentration. Two of these compounds (cetyldimethlyethylammonium bromide and methylbenzethonium chloride) also caused cell lysis at higher concentrations. However, only two of the compounds, namely, stearylamine and dimethyldioctadecylammonium bromide (DDAB), gave detectable transfection of BHK cells, and DDAB was far more effective than thearylamine. Because these and other experiments suggested that DDAB was more effective than the other compounds on a variety of cells, a more detailed analysis for only DDAB was conducted.

TABLE 1

Effectiveness of several cationic lipids in transfection of HeLa and BHK cells.

| Cationic lipid | (µg/ml) | Percent Cells Expressing | |
|---|---|---|---|
| | | HeLa | BHK |
| Cetyldimethylethylammonium bromide | 3 | 70 | 0 |
| | 6 | 76 | 0 |
| | 12 | 0* | 0* |
| Dimethyldioctadecyl-ammonium bromide | 6 | 50 | 30 |
| | 12 | 67 | 64 |
| Methylbenzethonium chloride | 3 | 23 | 0 |
| | 6 | 63 | 0 |
| | 12 | 0* | 0* |
| Stearylamine | 0.3 | 10 | 0 |
| | 3 | 60 | 5 |
| | 30 | 1 | 0.5 |

Cells were transfected with 5 µg pARG DNA bound to liposomes containing the indicated amounts of cationic lipids and 30 µg PtdEtn as described herein. Percentage of cells expressing was determined by indirect immunofluorescence microscopy at 6 hours after transfection. Liposomes formed with 30 µg/ml dipalmitoylphosphatidylethanolamine and 12 µg/ml of DDAB did not result in transfection of HeLa or BHK cells.
*indicates cell lysis To determine the transfection efficiency of liposomes containing DDAB on other cell types, several other cell lines were examined. Transfections into vTF-7 infected cells were conducted under conditions that were known to be optimal for BHK and HeLa cells. Determination of the percent of cells expressing was by indirect immunofluorescence microscopy. For AtT-20 cells (murine anterior pituitary) and RK-13 cells (rabbit kidney fibroblast), 50-60 percent of the cells expressing was obtained. For MDCK cells (Madin-Darby canine kidney epithelial), about 10% of the cells expressing were obtained. For other cells such as mouse L-cells and NIH 3T3 cells, the frequency of cells expressing was usually only about 5 percent. Variability in results obtained with cells that were poorly transfected suggested that a systematic analysis of DNA and lipid concentrations might well improve the transfection frequencies in these lines.

In addition to examining the percentage of cells expressing by direct counting under a fluorescence microscope, flow cytometry was also used to assess the accuracy of the direct cell counts and to examine the distribution of fluorescence intensities for the expressing cells. FIG. 1 shows examples of flow cytometry profiles for control (mock-transfected with DDAB liposomes)

Figure 1B:
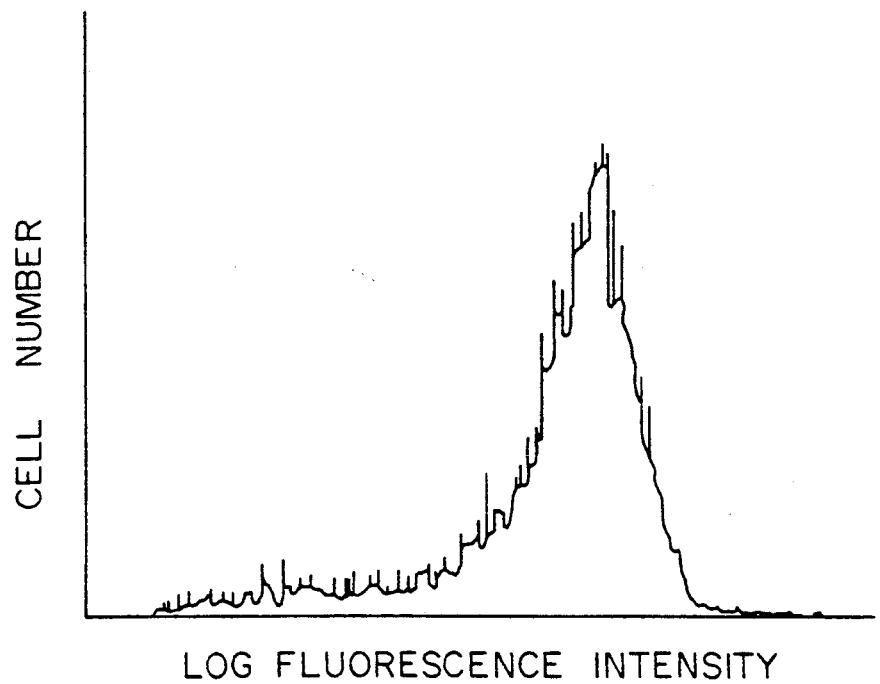

(FIG. 1A) and pARG transfected HeLa cells (FIG. 1B). Duplicate 6 cm dishes containing $2\times 10^6$ HeLa cells were infected with vTF-7 and then either transfected with 15 μg DNA encoding the VSV G protein (pARG) and 45 μl liposomes containing 18 μg DDAB or mock transfected with liposomes only. After six hours, cells were then fixed, immunostained for cell surface G protein and analyzed by flow cytometry as described in Whitt et al, *J. Virol.*, 63, 3569–3578, (1989).

The control cells fall in a sharp peak representing background fluorescence, while the majority of transfected cells (85%) are clearly positive for cell-surface expression of the VSV G protein. Using $CaPO_4$-DNA transfection, only 10% of the cells expressing (data not shown) was obtained. The heterogeneity in fluorescence of the positive cells probably reflects delivery of variable amounts of plasmid DNA into the cytoplasm of individual cells. The values obtained by direct counting paralleled those obtained by flow cytometry, but the flow cytometry values were generally somewhat higher. This difference probably reflects the greater sensitivity of the flow cytometry measurements.

EXAMPLE 7: EFFECT OF DDAB CONCENTRATION

Figure 2:
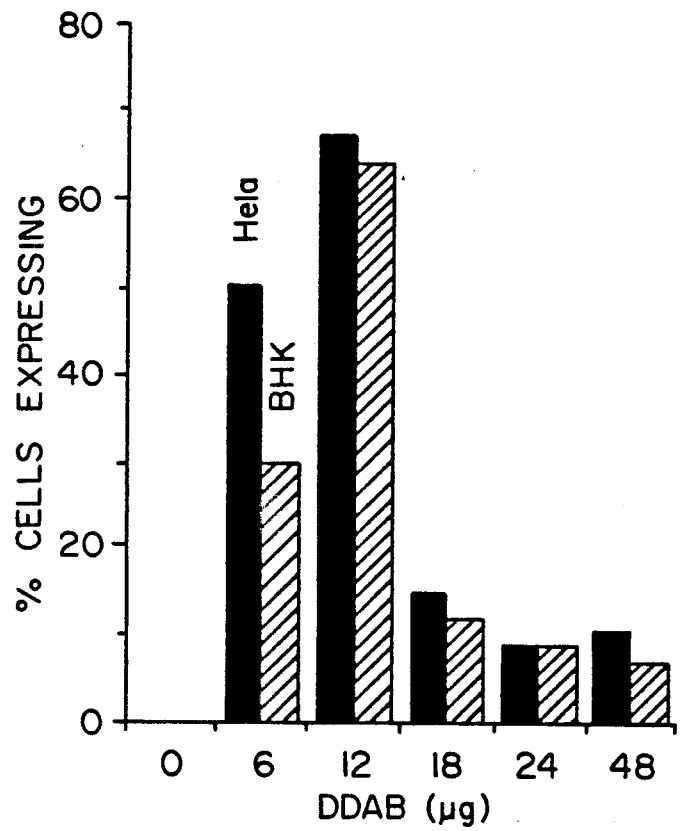
FIG. 2 is a series of bar graphs depicting the effect of DDAB concentration on expression frequency for pARG transfected for BHK cells and HeLa cells.

Liposomes containing a constant amount of PtdEtn and varying amounts of DDAB were prepared as described herein. Dishes containing $2\times 10^5$ HeLa or BHK cells on coverslips were infected with vTF-7 and then transfected with liposomes containing the indicated amounts of DDAB and 5 μg DNA. The percentage of cells expressing was determined by immunofluorescence microscopy. The results are depicted in FIG. 2. The concentration of PtdEtn was held constant at 30 μg/ml. Liposomes formed with PtdEtn alone gave no transfection. A final concentration of 12 μg/ml DDAB (30 μl of liposomes containing 0.4 mg/ml DDAB and 1 mg/ml PtdEtn added to 1 ml DMEM) appeared optimal and the percentage of cells expressing dropped off markedly at higher DDAB concentrations. HeLa cells with liposomes containing only DDAB were examined and it was found that these were only about half as effective as those containing PtdEtn (data not shown).

EXAMPLE 8: EFFECT OF DNA CONCENTRATION

Figure 3:
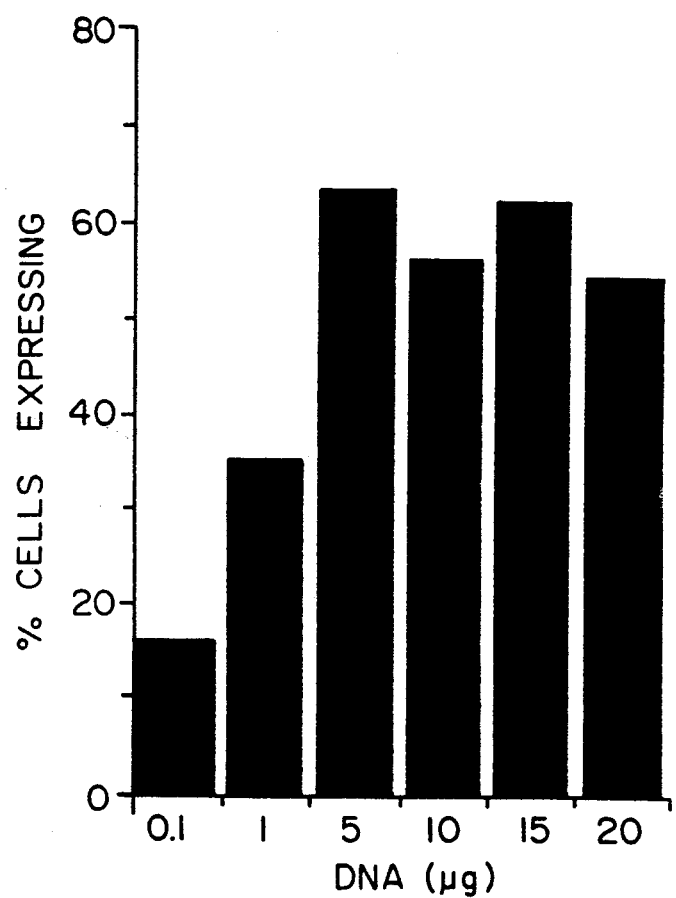
FIG. 3 is a series of bar graphs depicting the effect of DNA concentration on expression frequency for pARG transfected in BHK cells.

The effect of DNA concentration on the transfection frequency in BHK cells at the optimal lipid concentration as determined in FIG. 2 was examined. Dishes containing $2\times 10^5$ BHK cells on coverslips were transfected with the indicated amounts of DNA and 30 μl DDAB liposomes. The percentage of cells expressing was determined by immunofluorescence microscopy. The results are depicted in FIG. 3.

With as little as 0.1 μg of DNA, 18% of the cells expressing were obtained. This increased to a maximum of 62% with 5 μg of DNA in this experiment and was often as high as 80–90%. At higher DNA concentrations, there was a small decrease in number of cells expressing. Although the decrease appears insignificant in this experiment, more marked decreases at the high DNA concentrations with some liposome preparations were observed.

Figure 4:
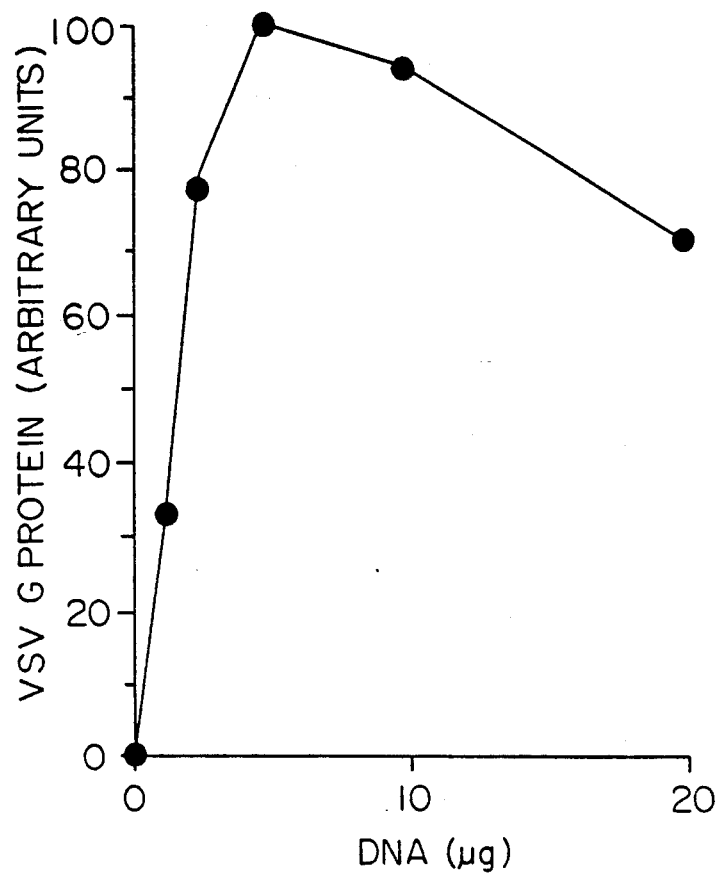
FIG. 4 is a graph showing the effect of DNA concentration on the rate of VSV G protein synthesis.

To test the effect of DNA concentration on the rate of protein synthesis directed by the transfected DNA, vTF-7 infected cells were transfected with the amounts of pARG DNA indicated (FIG. 3) and then pulse-labeled cells with [$^{35}$S]-methionine at four hours after transfection. This time was chosen because earlier experiments had shown that the rate of protein synthesis was already maximal by 4 hours. The VSV G protein was immunoprecipitated from the lysates and electrophoresed on an SDS-polyacrylamide gel. To ascertain the effect of DNA concentration on the rate of VSV G protein synthesis, six dishes containing $5\times 10^5$ Hela cells each were infected with vTF-7 and then transfected with 30 μl DDAB-liposomes and with certain amounts of DNA. The rates of VSV G protein synthesis were assessed by pulse-labeling with [$^{35}$S]-methionine, immunoprecipitation of the G protein, and autoradiography after gel electrophoresis. The results are depicted in FIG. 4.

Quantitation of the radiolabeled protein (FIG. 4) showed that the rate of protein synthesis reached a maximum with 5 μg of DNA and dropped off above this level. These results thus correlate well with those in FIG. 3, showing that transfection of 5 μg of DNA with 30 μl of DDAB liposomes gave an optimal percentage of cells expressing.

EXAMPLE 9: COMPARISON WITH DOTMA AND $CaPO_4$

Figure 5A:
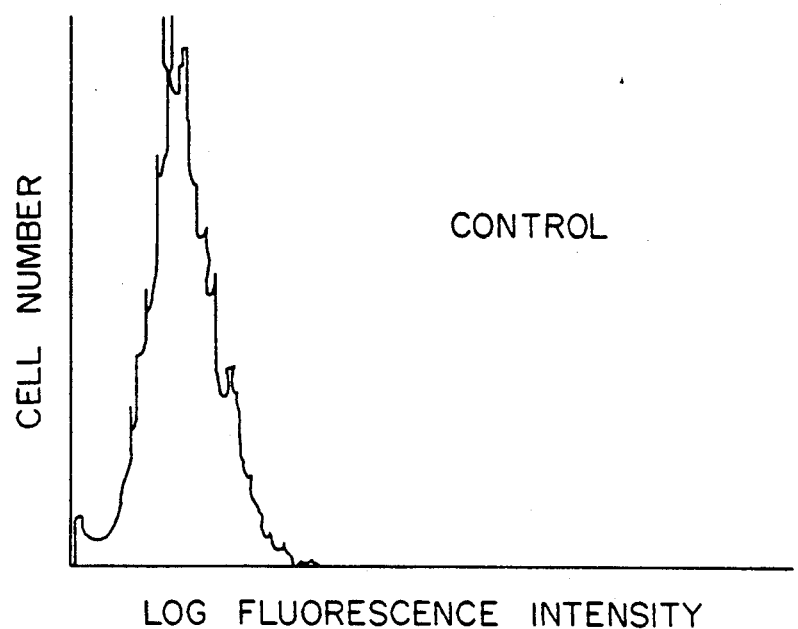
FIG. 5A, 5B, 5C, and 5D depict flow cytometry profiles for a control (mock transfected) (FIG. 5A), DDAB (FIG. 5B), "LIPOFECTIN" TM reagent that contains DOTMA (FIG. 5C) and CaPO4 (FIG. 5D).
Figure 5B:
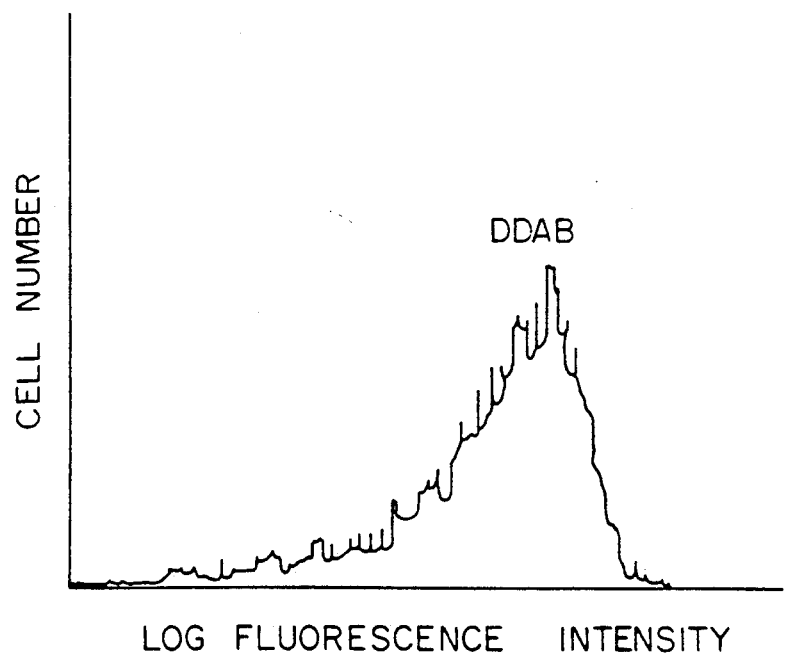
Figure 5C:
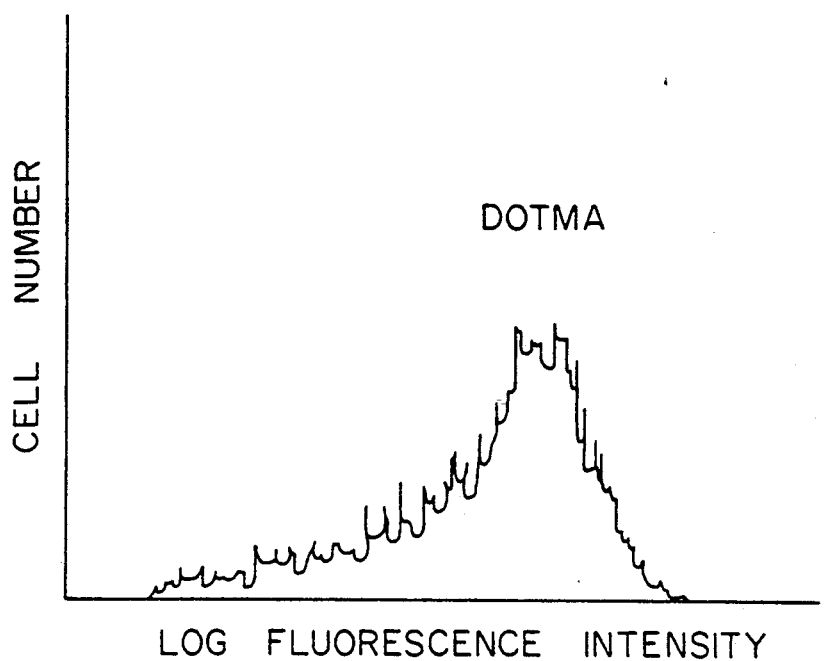
Figure 5D:
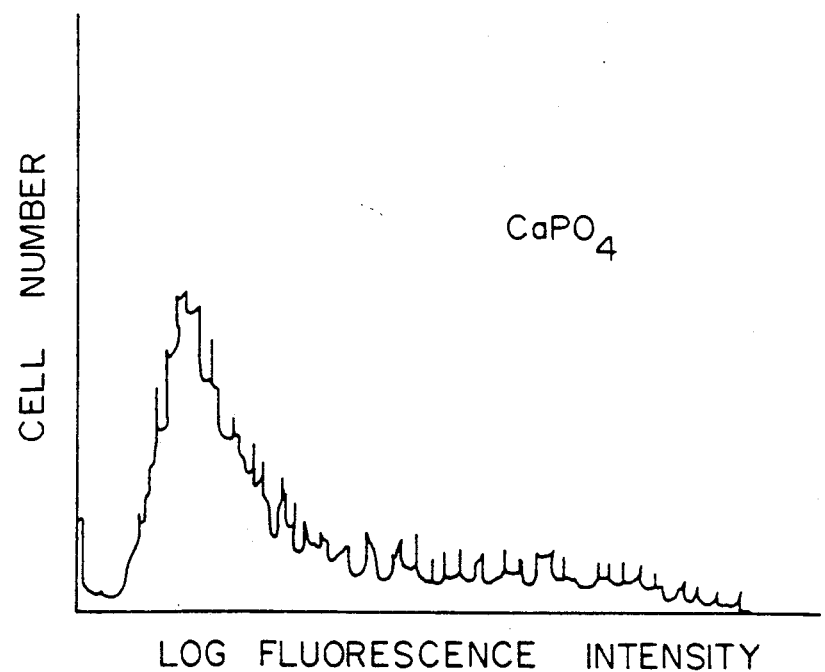

To determine how effective liposomes composed of DDAB were compared to those containing DOTMA, transfections of vTF-7-infected BHK cells with pARG and quantitated cell surface VSV G protein by flow cytometry were performed. A transfection with $CaPO_4$ precipitated DNA was also included for comparison. Four 6 cm dishes each containing $2\times 10^6$ BHK cells were infected with vTF-7 and were mock transfected (FIG. 5A), transfected with 15 μg of pARG DNA and 45 μl of DDAB-liposomes (FIG. 5B), 15 μg pARG DNA and 30 μl "LIPOFECTIN"™ reagent (DOTMA liposomes) (FIG. 5C), and with 15 μg pARG DNA as a $CaPO_4$ precipitate (FIG. 5D). At six hours after transfection, cells were fixed and stained for cell-surface G protein.

The flow cytometry profiles are shown in FIG. 5. Comparison with FIG. 5A (negative control of mock-transfected cells, DDAB liposomes) showed that DDAB-liposomes (FIG. 5B) gave 95% and DOTMA-liposomes (FIG. 5C) gave 85% of the cells expressing. A $CaPO_4$-precipitate of the same amount of DNA (FIG. 5D) yielded only 30% of the cells expressing. In other experiments DDAB-liposomes gave expression frequencies that were as much as two-fold higher than those obtained with DOTMA-liposomes.

RESULTS

Although liposomes containing all four lipids tested herein were effective in HeLa cells at some concentration, only one, dimethyldioctadecylammonium bromide, also mediated efficient DNA transfection into the cytoplasm of a variety of other cells including BHK, RK13, AtT20 (a pituitary cell line), and MDCK (Madin-Darby canine kidney), an epithelial cell line. The very high frequency of transient expression that was observed herein (up to 95% of the cells expressing) is presumably due to the requirement that the DNA only reach the cytoplasm. In other highly efficient transient systems such as monkey COS cells (Y. Gluzman, *Cell*, 23, 175–182, (1981)) the DNA must also cross the nuclear membrane to be expressed.

The mechanism by which liposomes containing positively charged lipids mediate transfection of DNA into animal cells is not presently understood. The DNA undoubtedly binds to the positively charged surface of the liposome, and residual positive charge then presumably mediates binding to negatively charged sialic acid residues on cell surfaces. The decrease that was observed in transfection frequencies at high DNA concentrations (FIG. 4) might be attributed to saturation of the positive charge on the liposomes.

Felgner et al, *Proc. Natl. Acad. Sci. USA*, 84, 7413-7417 (1987) presented evidence suggesting that liposomes containing DOTMA fuse with the plasma membrane. Because the plasmid DNA should be located on the outside of the liposomes, one would anticipate that fusion of the liposome with the plasma membrane would leave the DNA on the cell surface. An alternative possibility is that DNA bound to liposomes is taken up by endocytosis and that some fraction of the DNA is then released into the cytoplasm by an unknown mechanism. Given the uncertainty of how the DNA enters the cytoplasm, it is premature to speculate on why three of the cationic lipids tested worked well on HeLa cells, but not on BHK or other cells that were tested. One or more of these lipids may well be more effective than DDAB on some cell types.

The level of production of VSV G protein achieved in BHK cells was quantitated using DDAB transfection and the vaccinia/T7 system. Using immunoblots standardized with transfected with pARG synthesized the equivalent of $3 \times 10^6$ molecules VSV G protein per cell within six hours after transfection. The level of translation of mRNA transcribed by the T7 polymerase in vaccinia infected cells appears limited by the efficiency with which vaccinia virus enzymes cap the transcripts. The newly described use of the cap-independent translation initiation signal from EMC virus in conjunction with the vaccinia/T7 system will undoubtedly allow even higher levels of expression (O. Elroy-Stein, T. R. Fuerst and B. Moss, *Proc. Natl. Acad. Sci. USA*, 86, 6126-6130, (1989)).

An important aspect of the vaccinia/T7 system combined with DDAB mediated transfection, is that it permits a high efficiency of simultaneous expression of two or more genes. Using indirect immunofluorescence to monitor expression of two DNAs transfected simultaneously into HeLa cells, it was found that all (>95%) of the expressing cells were expressing both proteins at very similar levels. This feature of the system is very important to quantitative studies on protein-protein interactions where similar levels of each protein need to be made in all cells.

Given the high efficiency of DDAB containing liposomes in mediating cytoplasmic transfection in the vaccinia/T7 system, it is surprising that liposomes containing DDAB were reported to be ineffective in mediating transfection into cell nuclei (Felgner et al, *Proc. Natl. Acad. Sci. USA*, 84, 7413-7417 (1987) and F.L. Felgner and G.M. Reingold, *Nature*, 337, 387-389 (1989)). It is conceivable that liposomes containing DDAB are efficient only at delivering DNA into the cytoplasm. Arguing against this possibility is the fact that transient nuclear expression using DDAB containing liposomes and an SV40-based vector in monkey COS cells was observed. Transient nuclear expression of DNA in BHK cells was also observed. Transfection of DNA with liposomes containing DDAB is clearly ideal for many applications involving the vaccinia/T7 hybrid system, and will prove useful in many other applications as well.

It will be appreciated that the instant specification is set forth by way of illustration and not limitation, and that various modifications and changes may be made without departing from the spirit and scope of the present invention.

What is claimed is:

1. A liposome for introducing a nucleic acid into an animal cell comprising
   (a) a neutral lipid selected from the group consisting of lecithin, lysolecithin, lysophosphatidylethanolamine, phosphatidylserine, phosphatidylinositol, sphinogomyelin, cephalin, cardiolipin, phosphatidic acid, cerebrosides, dioleoylphosphatidylcholine, dipalmitoylphosphatidylcholine, dioleoylphosphatidylglycerol, dipalmitoylphosphatidylglycerol, palmitoyloleoylphosphatidylcholine, palmitoyloleoylphosphatidylethanolamine, diheptadecanoylphosphatidylethanolamine, dilauroylphosphatidylethanolamine, dimyristoylphosphatidylethanolamine, distearoylphosphatidylethanolamine, beta-linoleoyl-gamma-palmitoylphosphatidylethanolamine and beta-oleoyl-gamma-palmitoylphosphatidylethanolamine, and
   (b) a cationic lipid selection from the group consisting of dimethyldioctadecylammonium bromide, cetylidimethylethylammonium bromide, stearylamine and methylbenzethonium chloride, wherein the weight ratio of the cationic lipid to the neutral lipid is 6:30 to 12:30.

2. The liposome of claim 1, wherein the neutral lipid is dioleoylphosphatidylethanolamine.

3. The liposome of claim 1, wherein the cationic lipid is cetyldimethylethylammonium bromide.

4. The liposome of claim 1, wherein the cationic lipid is dimethyldioctadecylammonium bromide.

5. The liposome of claim 1, wherein the cationic lipid is stearylamine.

6. The liposome of claim 1, wherein the cationic lipid is methylbenzothonium chloride.

7. A composition comprising the liposome of claim 1, a nucleic acid, and an animal cell selected from the group consisting of arythrocytes, baby hamster kidney cells, AtI 20 cells, RK-13 cells, HeLa cells, Madin-Darby canine kidney cells and monkey COS cells.

8. A method for introducing RNA or DNA into an animal cell comprising (a) contacting said RNA or DNA with the liposome of claim 1 and then (b) contacting said liposome-RNA or liposome-DNA complex with an animal cell.

9. The method according to claim 8, wherein the method is carried out at a temperature of 37° C. for a period of three hours.

10. The method according to claim 8, wherein the animal cell is selected from the group consisting of arythrocytes, baby hamster kidney cells, AtI 20 cells, RK-13 cells, Heln cells, Madin-Darby canine kidney cells and monkey COS cells.

11. The method according to claim 9, wherein the animal cell is selected from the group consisting of erythrocytes, baby hamster kidney cells, AtI 20 cells, RK-13 cells, Heln cells, Madin-Darby canine kidney cells and monkey COS cells.

* * * * *